United States Patent [19]

Grabowski et al.

[11] Patent Number: 4,582,931

[45] Date of Patent: Apr. 15, 1986

[54] PREPARATION OF 2-DEUTERO-D-SERINE

[75] Inventors: Edward J. J. Grabowski; Paul J. Reider, both of Westfield, N.J.

[73] Assignee: Merck & Co., Inc., Rahway, N.J.

[21] Appl. No.: 685,945

[22] Filed: Dec. 24, 1984

[51] Int. Cl.$^4$ .......................................... C07C 101/30
[52] U.S. Cl. .................................. 562/567; 562/574; 548/239
[58] Field of Search ...................... 562/574, 575, 567

[56] References Cited

U.S. PATENT DOCUMENTS

| | | | |
|---|---|---|---|
| 2,867,654 | 1/1959 | Town | 562/575 |
| 3,956,367 | 5/1976 | Kollonitsch | 562/574 |
| 3,972,921 | 8/1976 | Dolling | 562/574 |
| 3,976,689 | 8/1976 | Reinhold | 562/574 |
| 4,028,405 | 6/1977 | Kollonitsch | 562/574 |
| 4,048,224 | 9/1977 | Chemerda | 562/574 |
| 4,096,180 | 6/1978 | Kollonitsch | 562/574 |

*Primary Examiner*—Michael L. Shippen
*Attorney, Agent, or Firm*—Daniel T. Szura; Hesna J. Pfeiffer; Julian S. Levitt

[57] ABSTRACT

A process for the preparation of 2-Deutero-D-serine and its fluorination is disclosed.

5 Claims, No Drawings

PREPARATION OF 2-DEUTERO-D-SERINE

BACKGROUND OF THE INVENTION

The present invention is concerned with preparation of deuteroserine used as an intermediate to prepare a fluorodeuteroalanine.

3-Fluoro-D,L and D-alanine-2d are known antibacterial agents. (See U.S. Pat. No. 3,956,367; U.S. Pat. No. 3,972,921; U.S. Pat. No. 4,031,231). Preparation of the non-deutero 3-fluoro-D,L-alanine from serine is known [(Isr. J. Chem 17, 53, (1978)]. No viable method of preparing 2-deutero-D-serine is available.

An efficient process for the preparation of 2-deutero-D-serine has been discovered and the serine has been selectively fluorinated to provide the aforesaid fluoralanine.

SUMMARY OF THE INVENTION

Preparation of 2-deuteroserine and its use to prepare a deutero fluoroalanine.

DETAILED DESCRIPTION OF THE INVENTION

The invention is embodied in a process for preparing 2-deutero-D-serine having the formula

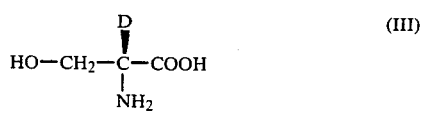

(A) deuteration of a 1,3-oxazoline carboxylate of the formula

wherein R and $R^1$ are independently selected from H, $C_1$–$C_{10}$ alkyl, allyl, aryl, aralkyl e.g. benzyl, or pyridyl by treatment with (a) a strong base to generate the anion of I followed by quenching with a deuterium source or (b) a tertiary amine base or alkoxide ($RO^-$) in excess of a deuterated alcohol $R^2OD$ wherein $R^2$ is $C_1$–$C_{10}$alkyl to obtain the product II having the formula

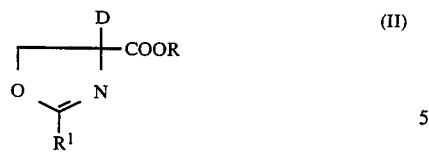

and (B) hydrolysis of II to obtain III.

The designation aryl includes hydrocarbonaryl having 5–10 carbon atoms e.g. phenyl, indanyl, naphthyl, and heteroaryl e.g. pyridyl and the like.

Preferred R groups are alkyl such as $CH_3$, n-hexyl, isopropyl and the like, and preferred $R^1$ groups are aryl such as phenyl, pyridyl, and the like.

Compound III has an asymmetric center. Thus, the product obtained is a racemate or racemic mixture. To obtain a stereospecific isomer of the III compound, the II product may be resolved via its diastereomeric salts with an appropriate optically active acid resolving agent. A preferred agent is d-(+)-α-bromocamphor-π-sulfonic acid, the isomer of III obtained being the D-form.

The strong base used in Step (A) (a) to form the anion of I may be varied, but should be derived from an acid which has no exchangeable protons, under normal protic conditions. Useful bases include trityllithium, t-butyllithium, phenyl sodium, dimsyl lithium, dimsyl sodium, amyl sodium in solvents such as tetrahydrofuran, 1,2-dimethoxyethane, t-butylmethylether, diethyl ether or toluene. This treatment with base is conducted at temperatures ranging from −100° C. to 0° C. The anion of I thus obtained is deuterated by quenching with deuterated carboxylic acids such as formic acid-O-D, acetic acid-O-D, propionic acid-O-D, other simple O-D carboxylic acids, $D_2SO_4$, $D_2O$ or i-Pro-D.

The step (A)(b) deuteration is carried out in a $C_1$–$C_6$alkanol-O-D solvent such as methanol-O-D, ethanol-O-D, propanol-O-D, iso-propanol-O-D, or similar alcohol-O-D using the corresponding alkoxide or a tertiary amine base such as triethylamine, diazobicycloundecane, DABCO, DBN or an anhydrous inorganic basic salt such as $K_2CO_3$, at temperatures of 0° C. to 100° C.

The resolution of II to obtain the D-isomer is effected with d-(+)-α-bromocamphor-π-sulfonic acid in an organic solvent such as acetonitrile, ethyl acetate, tetrahydrofuran, dichloromethane and toluene at temperatures between 0° C. and 40° C.

Alternatively, the resolution of II to obtain the L-isomer is effected with 1-(−)-α-bromocamphor-π-II-sulfonic acid. Hydrolysis of the L-oxazoline provides III as its L-isomer.

Hydrolysis of II to III is achieved using conventional acid systems.

Another embodiment of the invention is preparation of a fluoroalanine of the formula:

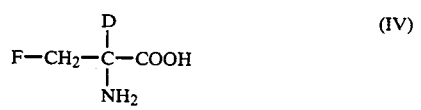

by (C) fluorodehydroxylating the formula III 2-deuteroserine using $SF_4$ in HF. The conditions for fluorodehydroxylation are generally described in the literature [see e.g. Kollonitsch et al, J. Org. Chem. 40, 3808–9 (1975); U.S. Pat. No. 4,325,961].

If racemic III is used, the IV compound obtained is a racemate; and it may be separated into its individual isomers, if desired, by conventional means.

A preferred procedure uses the III enantiomer to prepare the IV enantiomer the preferred form being the D-isomer.

A continuous process for preparing IV combines the (A), (B), and (C) steps set out above in sequence, with the resolution of II-step added if desired.

The following set of reaction equations illustrates the process of the present invention Steps 1 and 2 in the scheme are conventional and known to those skilled in the art.

SCHEME:

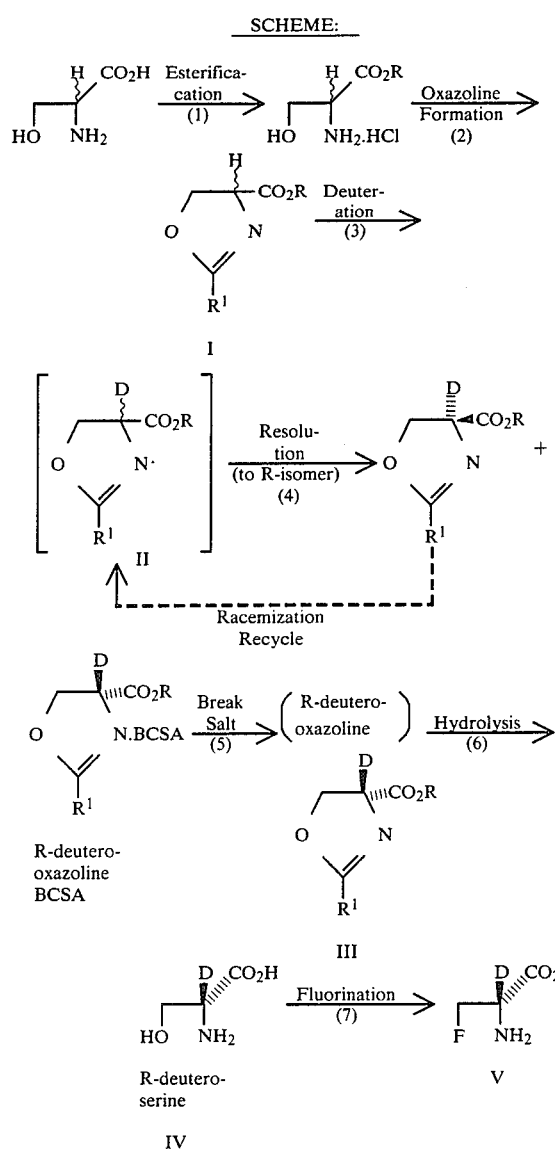

The following examples illustrate the processes of the invention. Temperatures are °C. unless otherwise indicated.

(A)

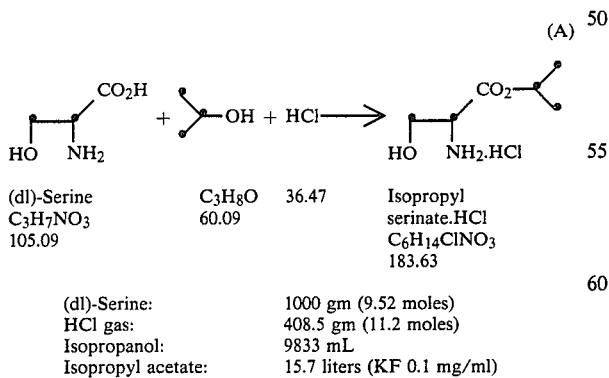

| (dl)-Serine | C$_3$H$_8$O | 36.47 | Isopropyl |
| --- | --- | --- | --- |
| C$_3$H$_7$NO$_3$ | 60.09 | | serinate.HCl |
| 105.09 | | | C$_6$H$_{14}$ClNO$_3$ |
| | | | 183.63 |

| (dl)-Serine: | 1000 gm (9.52 moles) |
| --- | --- |
| HCl gas: | 408.5 gm (11.2 moles) |
| Isopropanol: | 9833 mL |
| Isopropyl acetate: | 15.7 liters (KF 0.1 mg/ml) |

To a 12-liter 3-neck flask equipped with a mechanical stirrer, gas inlet tube, and a condenser fitted with a drying tube was added 9000 mL of isopropanol, followed by 1000 gm (9.52 moles) of dl-serine. Into the stirred slurry, initially at ambient temperature, HCl gas was then bubbled at a rate of about 3.2 moles/hour for 3.5 hours (total addition about 11.2 moles). The HCl addition is exothermic and is used to bring the reaction mixture to mild reflux. Upon completion of the HCl addition the condenser is removed, the gas inlet tube is raised above the surface of the mixture and closed off, and then 3000 mL of isopropanol-H$_2$O are removed by distillation at atmospheric pressure. Upon completion of the reaction the solution is cooled to about 60° C. and 6.5 liters of isopropyl acetate are added as rapidly as is convenient. The mixture is then cooled to 20° C. and aged for 3 hours. The precipitated isopropyl serinate hydrochloride is filtered, washed with 5 liters of 5:1 isopropyl acetate:isopropyl alcohol, 5 liters of isopropyl acetate and then vacuum dried at 50° C. for 12 hours.

Yield 1.607 kg (92%). (M.p. 141°–143° C.).

Analysis for C$_6$H$_{14}$ClNO$_3$:

Calculated: C, 39.20; H, 7.68; N, 7.63; Cl, 19.3. Found: C, 39.21; H, 7.64; N, 7.68; Cl, 19.08.

(B) (±)-Isopropyl 2-phenyl-2-oxazoline-4-carboxylate

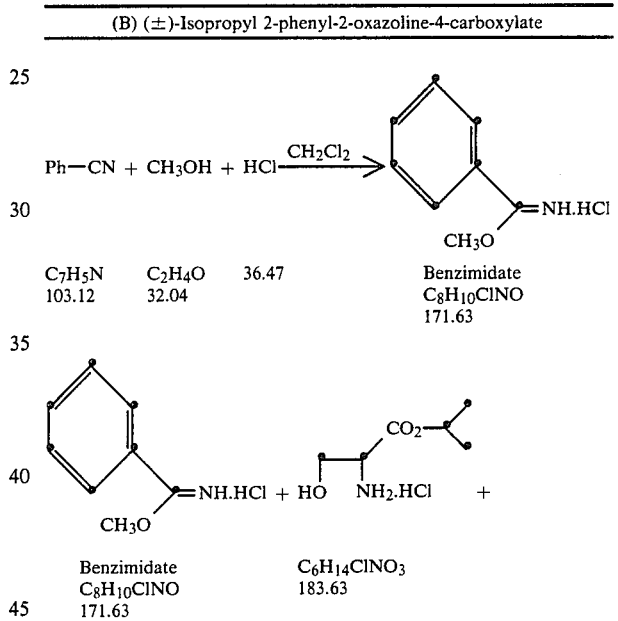

| C$_7$H$_5$N | C$_2$H$_4$O | 36.47 | Benzimidate |
| --- | --- | --- | --- |
| 103.12 | 32.04 | | C$_8$H$_{10}$ClNO |
| | | | 171.63 |

| Benzimidate | C$_6$H$_{14}$ClNO$_3$ |
| --- | --- |
| C$_8$H$_{10}$ClNO | 183.63 |
| 171.63 | |

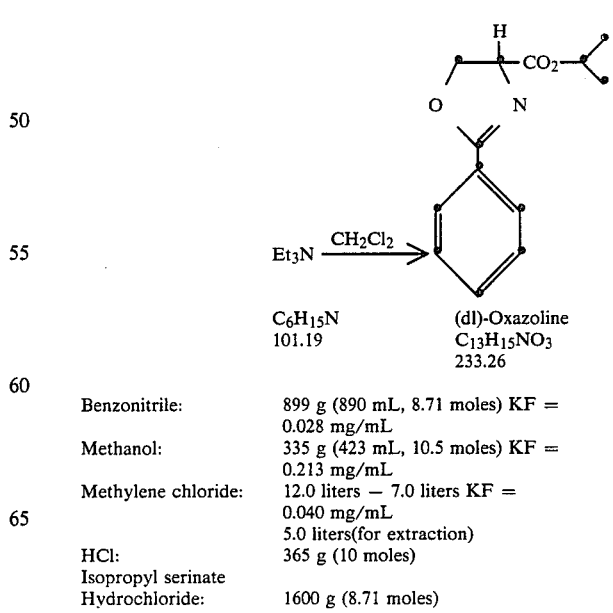

| C$_6$H$_{15}$N | (dl)-Oxazoline |
| --- | --- |
| 101.19 | C$_{13}$H$_{15}$NO$_3$ |
| | 233.26 |

| Benzonitrile: | 899 g (890 mL, 8.71 moles) KF = 0.028 mg/mL |
| --- | --- |
| Methanol: | 335 g (423 mL, 10.5 moles) KF = 0.213 mg/mL |
| Methylene chloride: | 12.0 liters − 7.0 liters KF = 0.040 mg/mL |
| | 5.0 liters(for extraction) |
| HCl: | 365 g (10 moles) |
| Isopropyl serinate Hydrochloride: | 1600 g (8.71 moles) |

-continued

| (B) (±)-Isopropyl 2-phenyl-2-oxazoline-4-carboxylate | |
| --- | --- |
| Triethylamine: | 1254 mL (9.0 moles) KF = 0.021 mg/mL |
| Hexanes: | 25.0 liters KF = 0.035 mg/mL |
| H$_2$O: | 12.0 liters |
| Na$_2$SO$_4$ (anhy): | 200 gm |
| Darco G-60: | 80 gm |

Into a 12-liter 3-neck flask equipped with a mechanical stirrer, gas inlet tube, and a condenser are charged 890 mL (8.71 moles) benzonitrile, 423 mL (10.46 moles) methanol, and 215 mL of methylene chloride. Into the stirred solution, initially at ambient temperature, is bubbled HCl gas at a rate of about 3.6 moles/hour for 2.75 hours (total addition about 365 g–10 moles). During the addition of HCl an internal temperature of 20°–25° C. is maintained. Approximately 2 hours into the HCl addition solid imidate.HCl begins to precipitate. At this time an additional 215 mL of CH$_2$Cl$_2$ is added to facilitate stirring. The mixture is stirred at 20°–25° C. until a GC assay indicates less than 3% residual benzonitrile. CH$_2$Cl$_2$ (1000 mL) is added to the mixture and then it is distilled off at less than or equal to 20° C. (vacuum) in order to remove any residual HCl. This operation is repeated a second time to insure complete removal of free HCl. The resulting methyl benzimidate suspension is diluted with 4500 mL of CH$_2$Cl$_2$ and then isopropyl serinate.HCl (1600 g, 8.71 moles) is charged. While maintaining an internal temperature of 20°–25° C. (with cooling) 1254 mL (9.0 moles) of triethylamine is added over 30 minutes. The white suspension is stirred at 20°–25° C. for about 8 hours. Upon completion of the reaction the suspension is diluted with 5.0 liters of CH$_2$Cl$_2$ and washed with 6.0 liters of H$_2$O. After separation of the layers the CH$_2$Cl$_2$ is washed with an additional 6.0 liters of H$_2$O. The organic layer is then dried over Na$_2$SO$_4$ (200 gm) until the water content is less than or equal to 1.5 mg/mL. The dried methylene chloride solution is vacuum concentrated at or below 25° C. to a small stirrable volume. To this solution is added 4.0 liters of hexane and the mixture is concentrated keeping the temperature between 30°–50° C. The oxazoline is then dissolved in 16.0 liters of hot hexane (about 60° C.). The solution is treated with 80 gm Darco G-60, cooled to 30°–35° C., and filtered. The Darco is washed with 2 liters of about 35° hexane and the filtrates are combined. The volume of the hexane solution is adjusted to about 11 liters by vacuum distillation. The inherent cooling is used to lower the temperature to 10°–15° C. This temperature is maintained until the final volume of 11.0 liters is reached. At this point the temperature is lowered with external cooling to −5° C. and held for 3 hours to allow complete crystallization. The cold suspension is filtered, washed with 2.0 liters of less than 0° C. hexane and vacuum dried at less than or equal to 24° C. The mother liquors are concentrated in vacuo to a volume of about 2.0 liters. Cooling to −5° C. produces a second crop which is filtered, washed with 300 mL of less than 0° C. hexane. Yield: 1st crop: 64% 2nd crop: 8%. After checking melting points the crops are combined to yield 1460 g (6.76 moles) of oxazoline. (M.p. 40°–42°; titration (HClO$_4$) greater than 97%.)

Analysis for C$_{13}$H$_{15}$NO$_3$: Calculated: C, 66.94; H, 6.48; N, 6.00. Found: C, 66.57; H, 6.45; N, 6.01.

| (C) Triphenylmethyllithium | |
| --- | --- |
| Ph$_3$CH + n-BuLi $\xrightarrow{\text{THF}}$ Ph$_3$CLi + C$_4$H$_{10}$ | |
| C$_{19}$H$_{16}$ | C$_{19}$H$_{15}$Li |
| 244.34 | 250.27 |
| Triphenylmethane: | 733 g (3.00 moles) |
| n-Butyllithium: | 1.733 liters (2.67 moles, 1.54 M in hexane, d = 0.680) |
| Tetrahydrofuran: | 3 liters (KF = 26 μg/ml) |

A 12-liter 3-neck flask was equipped with a mechanical stirrer, a 1 to 2 liter pressure equalizing addition funnel, a nitrogen inlet and a thermometer. The entire system was dried with a heat gun under a stream of dry nitrogen. After the system had cooled to room temperature, triphenylmethane (733 g, 3.00 moles) was charged under a positive N$_2$ stream. Tetrahydrofuran (3.0 liters) was added; the triphenylmethane dissolved. The reaction mixture was cooled in an ice/water bath to an internal temperature of 10° C. n-Butyllithium [1.733 liters of 1.54M (2.67 moles)] was transferred to the addition funnel by cannula. The n-butyllithium was added over 1.25 hours such that the internal temperature remained at 10°–15°. On completion of the addition, the addition funnel was flushed with a minimal amount of THF and the reaction mixture stirred at 15° (internal temperature) for 1.5 hours. The reaction was then cooled to −70° (internal temperature) in a dry ice/acetone bath.

(D) Isopropyl (R,S)—4-deutero-2-phenyl-2-oxazoline-4-carboxylate

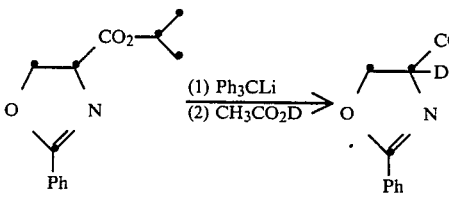

| Isopropyl (R,S)—2-Phenyl-2-oxazoline-4-carboxylate: | 500 g (2.14 moles) |
| --- | --- |
| Triphenylmethyllithium | (2.67 moles) - prepared in previous experimental |
| Acetic acid-O—d: | 196 g (3.21 moles, 98.5% D) |
| Tetrahydrofuran: | 500 ml (KF = 25 μg/ml) |
| Ethyl acetate: | 8 liters |
| Water: | 5 liters |
| Sodium sulfate, anhydrous: | 1.1 kg (granular) |
| Acetonitrile: | 6 liters (KF = 35 μg/ml) |

A solution of the oxazoline (500 g, 2.14 moles) in 500 ml of THF was prepared (KF = 136 μg/ml).

To the triphenylmethyllithium solution prepared in the previous experimental, at −70°, was added the oxazoline solution in THF, at a rate to maintain the internal temperature below −60°. This required 30 minutes. On completion of the addition, the addition funnel was rinsed with a minimal amount of dry THF and the reaction mixture stirred at −60° to −70° for 0.5 hour.

Acetic acid-O-d (196 g, 3.21 moles) was transferred to the addition funnel by cannula and added to the reaction mixture over 15 minutes, keeping the internal temperature below −60°. On completion of the addition, the reaction mixture was warmed to room temperature with stirring. The reaction mixture was diluted with 5 liters of ethyl acetate and transferred to an extractor. Water (5 liters) was added, the system stirred for 15 minutes and the layers separated. The aqueous phase was washed with an additional 3 liters of ethyl acetate. The combined organics (ca. 16 liters) were dried with 1.1 kg of granular, anhydrous sodium sulfate. The ethyl acetate solution was filtered and the sodium sulfate washed with 2 liters of ethyl acetate. The organic solution was concentrated to ca. 2 liters (T less than or equal to 25°). Acetonitrile (3 liters) was added. The reaction mixture was again concentrated to 2 liters keeping the internal temperature ca. 20°. Following concentration acetonitrile was added (ca. 3 liters) to a final volume of 5 liters. This solution (KF=360 μg/ml) was carried into the resolution.

(E) Isopropyl (R)—4-Deutero-2-phenyloxazolinium-4-carboxylate d-α-Bromocamphor- -sulfonium salt

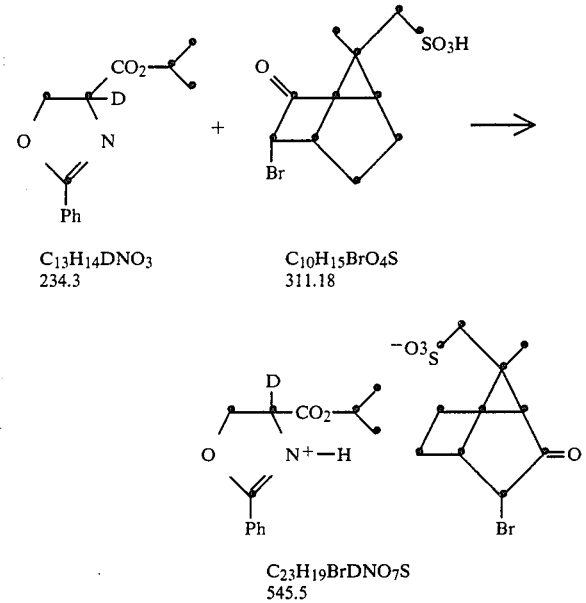

$C_{13}H_{14}DNO_3$
234.3

$C_{10}H_{15}BrO_4S$
311.18

$C_{23}H_{19}BrDNO_7S$
545.5

Isopropyl (R,S)—4-Deutero-2-phenyl-2-oxazoline-4-carboxylate acetonitrile solution from previous experimental: c. 5 liters (0.37 M in oxazoline, 1.85 moles also contains triphenylmethane, KF = 360 μg/ml)
d-(+)-α-Bromocamphor-π-sulfonic Acid, 0.5 M in acetonitrile: 1.86 liters (0.93 mole, KF = 3–4 mg/ml)

The acetonitrile solution of the oxazoline under $N_2$ was in a 3-neck 12-liter flask equipped with a mechanical stirrer, an addition funnel with a drying tube, and a thermometer, and cooled with a water bath. An aliquot of the solution was removed for perchloric acid titration and HPLC assay. The charge of bromocamphorsulfonic acid was 0.5 equivalents based on the HPLC assay. An acetonitrile solution of bromocamphorsulfonic acid (1.86 liters, 0.5M, KF=3–4 mg/ml) was added over 15 minutes, maintaining an internal temperature of 20°–30°. The reaction was stirred for 2 hours after the completion of the addition. The salt was filtered, washed with 2 liters of acetonitrile, and dried, in vacuo, overnight at 35° to yield 350 g (0.641 mole, 30%) of the (R)-oxazoline-d-bromocamphorsulfonate. D content=95.4%; R/S ratio=99.5/0.5.

(F) (R)—2-Deutero serine

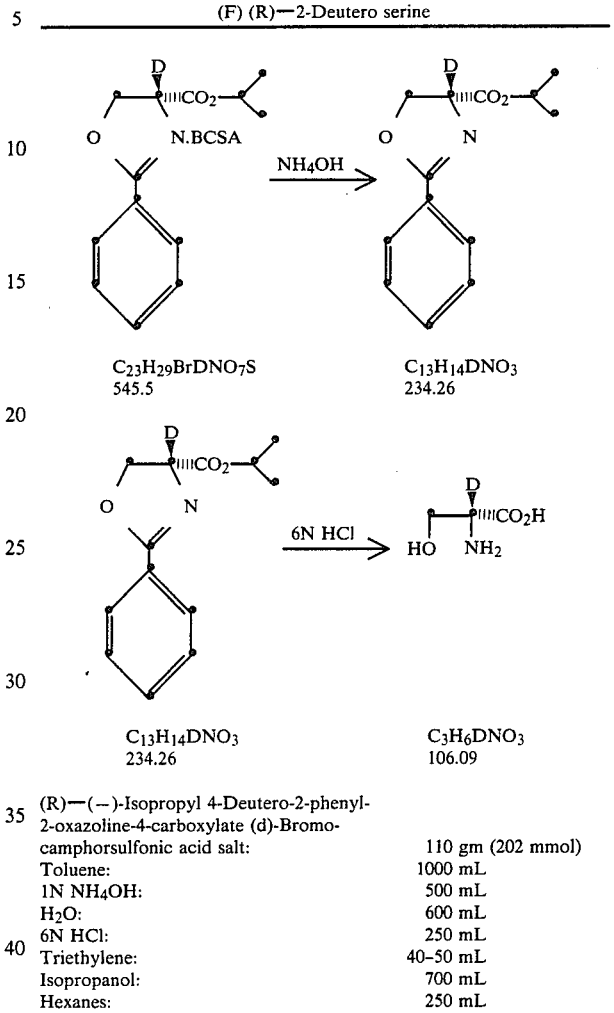

$C_{23}H_{29}BrDNO_7S$
545.5

$C_{13}H_{14}DNO_3$
234.26

$C_{13}H_{14}DNO_3$
234.26

$C_3H_6DNO_3$
106.09

(R)—(−)-Isopropyl 4-Deutero-2-phenyl-2-oxazoline-4-carboxylate (d)-Bromocamphorsulfonic acid salt:

| | |
|---|---|
| (R)-(−)-Isopropyl 4-Deutero-2-phenyl-2-oxazoline-4-carboxylate (d)-Bromocamphorsulfonic acid salt: | 110 gm (202 mmol) |
| Toluene: | 1000 mL |
| 1N NH₄OH: | 500 mL |
| H₂O: | 600 mL |
| 6N HCl: | 250 mL |
| Triethylene: | 40–50 mL |
| Isopropanol: | 700 mL |
| Hexanes: | 250 mL |

To a 2-liter separatory funnel was added 100 gm (202 mmol) of (R)-oxazoline bromocamphorsulfonic acid salt, 200 mL toluene, and 200 mL of 2N aqueous NH₄OH. The mixture was thorougly mixed and the layers separated. The lower (aqueous) layer was then reextracted with 200 mL of toluene. Removal of the aqueous layer was followed by combining both toluene extracts in the separatory funnel. The combined toluene extracts were washed with 200 mL H₂O and then placed in a 2-liter 3-neck flask, equipped with a mechanical stirrer, vacuum distillation head, and a stopcock. The volume was reduced by distilling (vacuum) 200 mL of toluene. To the resulting toluene solution of the free (R)-oxazoline was added 250 mL of 6N HCl. After replacing the distillation head with a condenser the two phase mixture was heated to reflux for 2.5 hours and then cooled to about 25° C. The reaction mixture was transferred to a 1000 mL separatory funnel and the layers separated. The aqueous layer was concentrated to a volume of 50 mL while maintaining an internal temperature less than or equal to 50° C. (vacuum). H₂O (200 mL) was then added and the concentration to 50 mL repeated. When titration (HCl, CO₂H, NH₃⁻Cl⁻, Cl⁻) indicated less than 50% excess HCl, the aqueous solution of serine.HCl was diluted to a volume of 100 mL with H₂O and the pH adjusted to 5.1 by the addition (with stirring) of Et₃N (about 40–50 mL). The internal temperature was maintained below 20° C. by external cooling during the pH adjustment. When the aqueous solution was at pH 5.1 product was crystallized by the addition, with stirring of 500 mL of isopropanol. The suspension was aged at about 10° for 1 hour and then filtered. The cake was washed with i-propanol (200 mL), hexane (250 mL), and then dried under vacuum. Isolated yield 19.7 g (92%). Spinco (97%), m.p. (dec) 219°–220° C., HPLC (greater than 98%), KF (less than 0.3%), LOD (less than 0.1%), mass spec. (greater than 95% deuterated).

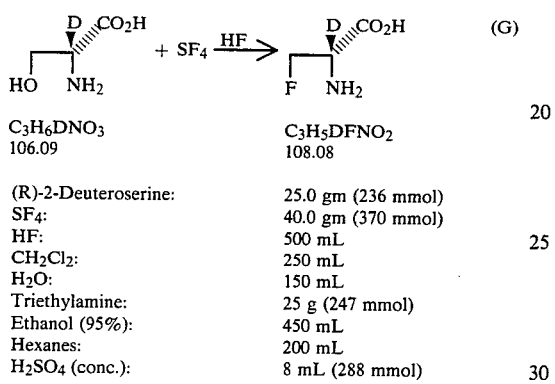

(R)-2-Deuteroserine: 25.0 gm (236 mmol)
SF₄: 40.0 gm (370 mmol)
HF: 500 mL
CH₂Cl₂: 250 mL
H₂O: 150 mL
Triethylamine: 25 g (247 mmol)
Ethanol (95%): 450 mL
Hexanes: 200 mL
H₂SO₄ (conc.): 8 mL (288 mmol)

Into a 1000 mL stainless steel cylinder equipped with a stainless steel sparge (set 1" above bottom) and a needle valve was placed 25.0 gm (236 mmol) of (R)-2-deuteroserine. The system was sealed, evacuated, and cooled to −40° C. Liquid HF (500 mL) was introduced through the sparge and the system agitated to insure dissolution of the serine. SF₄ (gas)—40 gm (370 mmol) was then rapidly introduced subsurface through the sparge at a rate of about 2 gm/second. The inlet valve on the sparge was then closed and the mixture allowed to warm to 0° C. When the reaction mixture reached 0° C. (approximately 3 hours) the outlet valve was carefully opened and the HF vented to a KOH scrubber. After the nitrogen flow had been running for 1.0 hour the system was sealed. A mixture of H₂SO₄ (8 mL) and H₂O (4 mL) was then blown, under pressure, into the vessel—subsurface. At this point the outlet valve was carefully vented and HF removal was continued. The HF was removed until the volume became small but stirrable. CH₂Cl₂ (250 mL) was then introduced into the reaction vessel through the sparge by applying vacuum to the outlet valve. CH₂Cl₂ (200 mL) was distilled at reduced pressure to insure removal of any residual HF. The resulting suspension of MK-0641 sulfate in 50 mL CH₂Cl₂ was treated with 150 mL H₂O and vacuum distillation was resumed to remove the remaining CH₂Cl₂. The resulting aqueous solution was then treated with Et₃N (25 g, 247 mmol), while maintaining an internal temperature below 20° C., until the pH reached 5.2. Ethanol (450 mL of 95%) was added to complete the crystallization. The resulting suspension was cooled to 5° C. and aged for 1 hour. The MK-0641 was isolated by filtration and the cake was washed with 95% ethanol (200 mL) and vacuum dried. Yield 20.4 g (80%); LC 99.3% MK-0641; deuterium greater than or equal to 98%, GC (optical purity) greater than 99.7%.

Analysis for C₃H₅DFNO₂: Calculated: C, 33.34; H, 5.60; N, 12.96. Found: C, 33.34; H, 5.61; N, 12.96.
[α]₃₆₅²⁵ = 305.4° (aq. CuSO₄ buffer)
[α]₄₀₅²⁵ = 211.1° (aq. CuSO₄ buffer)
GC (Chiral): greater than 99.7% S-isomer

EXAMPLE 2

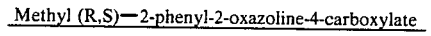

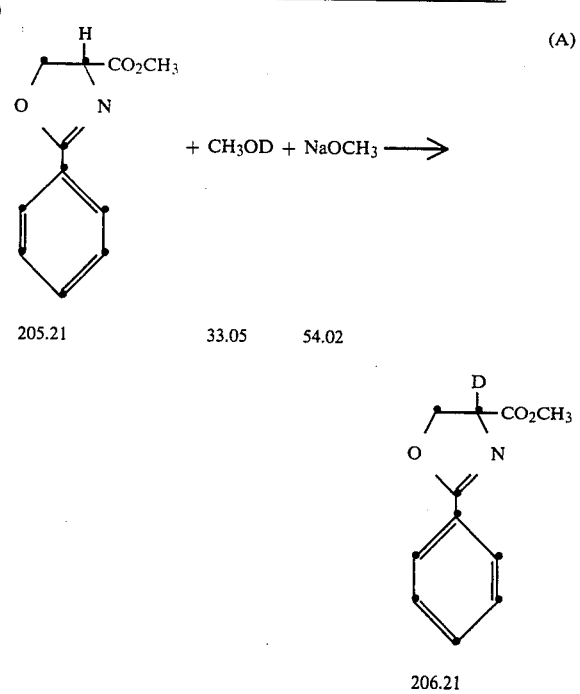

A mixture of 1.307 g (6.37 mmol) methyl (R,S)-2-phenyl-2-oxazoline-4-carboxylate, 5 mL CH₃OD (123 mmol), and 70 mg sodium methoxide (20 mole %) was stirred at 25° C. for 2 hours and then concentrated to an oil. The oily residue was dissolved in 5 mL of fresh CH₃OD and stirred at 25° C. for 2 hours. The resulting mixture was cooled to 0° C., treated with 75 mg (0.76 mmol) of concentrated sulfuric acid, and then concentrated to an oil. The resulting oxazoline (1.21 g, 92%) was greater than or equal to 98% deuterated by 250 MHz NMR.

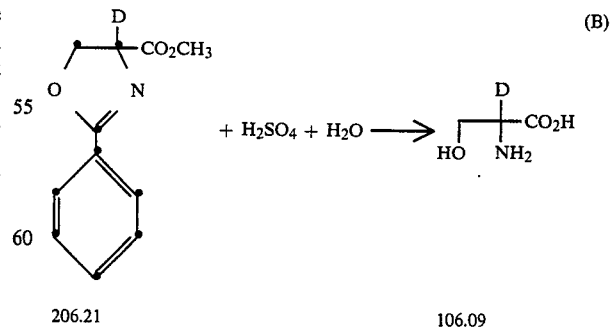

The crude oxazoline from the previous example was treated with 1.248 g (12.74 mmol) of H₂SO₄ and 15 mL H₂O and heated at 100° C. for 20 hours. After cooling to 25° C. the insoluble benzoic acid was removed by filtration and the aqueous filtrate placed on Dowex-50 (acid cycle). Elution with 1N NH₄OH followed by vacuum concentration produced the amino acid (450 mg, 67% based on protio oxazoline) as crystalline material which was greater than 98% deuterated.

Claims to the invention follow.

What is claimed is:

1. A procss for preparing 2-deuteroserine having the formula:

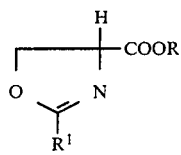

III by (A) deuteration of a 1,3-oxazoline of the formula:

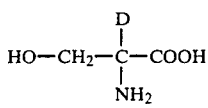

I wherein R and R¹ are independently selected from H, $C_1$-$C_{10}$alkyl, allyl, aryl, aralkyl and pyridyl by treatment with (a) a strong base followed by quenching with a deuterium source or (b) a tertiary amine base or alkoxide —$R^2O$ in an excess of a deuterated $C_1$-$C_6$alkanol, $R^2$—OD wherein $R^2$ is $C_1$-$C_{10}$alkyl, to obtain the product

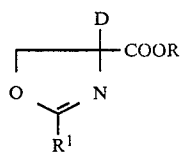

II and (B) hydrolysis of II to obtain III.

2. The process of claim 1 wherein II is resolved to obtain its D-isomer which is then hydrolyzed to obtain the D-isomer of III.

3. The process of claim 1 wherein R is $C_1$-$C_6$ alkyl and R¹ is aryl.

4. The process of claim 1 wherein deuteration is effected by treatment (a).

5. The process of claim 1 wherein deuteration is effected by treatment (b).

* * * * *